(12) United States Patent
Ryan et al.

(10) Patent No.: US 10,120,979 B2
(45) Date of Patent: Nov. 6, 2018

(54) PREDICTING GLUCOSE TRENDS FOR POPULATION MANAGEMENT

(71) Applicant: CERNER INNOVATION, INC., Kansas City, KS (US)

(72) Inventors: Hugh H. Ryan, Lee's Summit, MO (US); Megan Kathleen Quick, Kansas City, MO (US); Daniel Craig Crough, Overland Park, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 771 days.

(21) Appl. No.: 14/581,052

(22) Filed: Dec. 23, 2014

(65) Prior Publication Data

US 2016/0180040 A1 Jun. 23, 2016

(51) Int. Cl.
*G06F 19/00* (2018.01)
*G16H 50/20* (2018.01)

(52) U.S. Cl.
CPC ........... *G06F 19/345* (2013.01); *G16H 50/20* (2018.01)

(58) Field of Classification Search
None
See application file for complete search history.

(56) References Cited

U.S. PATENT DOCUMENTS

| | | | | |
|---|---|---|---|---|
| 5,251,126 A | * | 10/1993 | Kahn | G01N 35/00871 128/923 |
| 2002/0123906 A1 | * | 9/2002 | Goetzke | G06F 19/3437 705/2 |
| 2008/0046292 A1 | * | 2/2008 | Myers | G06F 17/30557 705/3 |

(Continued)

FOREIGN PATENT DOCUMENTS

| EP | 0483595 B1 | * | 5/1992 | ....... G01N 35/00871 |
|---|---|---|---|---|
| WO | WO 2006055630 A2 | * | 5/2006 | ........... G06F 19/328 |
| WO | WO 2006133368 A2 | * | 12/2006 | ........... G06F 19/345 |

OTHER PUBLICATIONS

Plis K, Bunescu R, Marling C, Shubrook J, Schwartz F. "A machine learning approach to predicting blood glucose levels for diabetes management". Modern Artificial Intelligence for Health Analytics. Papers from the AAAI-14. Mar. 2014.*

(Continued)

*Primary Examiner* — Alan Chen
(74) *Attorney, Agent, or Firm* — Shook, Hardy and Bacon LLP

(57) ABSTRACT

Computerized systems and methods facilitate preventing dangerous blood glucose levels using a predictive model to predict whether a particular patient is trending to have dangerous blood glucose levels. The predictive model may be built using logistic or linear regression models incorporating glucose data associated with a plurality of patients received from a plurality of sources. The glucose data may include context data and demographic data associated with the glucose data and the plurality of patients. The predictive model may be employed to predict a likelihood of a particular patient to have dangerous blood glucose levels. Based on the likelihood, the prediction and one or more interventions are communicated to a care team or the patient. The one or more interventions may be incorporated into a clinical device workflow associated with a clinician on the care team or the patient.

18 Claims, 7 Drawing Sheets

(56) References Cited

U.S. PATENT DOCUMENTS

| | | | |
|---|---|---|---|
| 2008/0120267 A1* | 5/2008 | Chen | G06N 99/005 706/61 |
| 2008/0221923 A1* | 9/2008 | Shogan | G06Q 50/22 705/2 |
| 2010/0292634 A1* | 11/2010 | Kircher, Jr. | A61B 5/14532 604/66 |
| 2010/0312581 A1* | 12/2010 | Wachtell | G06F 19/327 705/3 |
| 2010/0324936 A1* | 12/2010 | Vishnubhatla | G06F 19/328 705/3 |
| 2011/0093288 A1* | 4/2011 | Soto | G06F 19/3431 705/2 |
| 2011/0225112 A1* | 9/2011 | Cameron | G06F 19/3456 706/20 |
| 2012/0065987 A1* | 3/2012 | Farooq | G06F 19/327 705/2 |
| 2013/0197942 A1* | 8/2013 | Chiu | G06F 19/3431 705/3 |
| 2013/0262357 A1* | 10/2013 | Amarasingham | G06F 19/345 706/21 |
| 2014/0012117 A1* | 1/2014 | Mensinger | G16H 40/40 600/365 |
| 2014/0118138 A1* | 5/2014 | Cobelli | A61B 5/746 340/539.12 |
| 2014/0156304 A1* | 6/2014 | Michon | G06Q 50/22 705/3 |
| 2015/0006456 A1* | 1/2015 | Sudharsan | G06N 5/048 706/46 |
| 2015/0018633 A1* | 1/2015 | Kovachev | A61B 5/0022 600/301 |
| 2017/0249445 A1* | 8/2017 | Devries | G06F 19/3475 |

OTHER PUBLICATIONS

Makam AN, Nguyen OK, Moore B, Ma Y, Amarasingham R. "Identifying patients with diabetes and the earliest date of diagnosis in real time: an electronic health record case-finding algorithm". BMC medical informatics and decision making. Aug. 1, 2013;13(1):81.*

Bunescu R, Struble N, Marling C, Shubrook J, Schwartz F. "Blood glucose level prediction using physiological models and support vector regression". InMachine Learning and Applications (ICMLA), 2013 12th International Conference on Dec. 4, 2013 (vol. 1, pp. 135-140). IEEE.*

Kumar, Anil R., and Paul B. Kaplowitz. "Patient age, race and the type of diabetes have an impact on the presenting symptoms, latency before diagnosis and laboratory abnormalities at time of diagnosis of diabetes mellitus in children." Journal of Clinical Fesearch in Pediatric Endocrinology, 2009;1(5):227-32. doi: 10.4274/jcrpe.v1i5.227. Epub 2009.*

Poddar R, Andrews JT, Shukla P, Sen P. "Non-invasive glucose monitoring techniques: A review and current trends". arXiv preprint arXiv:0810.5755. Oct. 31, 2008, pp. 2-6, 32-34.*

Skyler JS, Skyler DL, Seigler DE, O'Sullivan MJ. "Algorithms for adjustment of insulin dosage by patients who monitor blood glucose". Diabetes Care. Mar. 1, 1981;4(2):311-8.*

Purcell, Sarah. "Beverage Consumption in Children with Diabetes Mellitus: Weekend Versus Weekday Intake." (2012), PDF pp. 1, 5-7, 13, 17-21.*

Steve Olson, Rapporteur. "The Role of Human Factors in Home Health Care: Workshop Summary", The National Academies Press (2010), pp. 145-200.*

Powers, Margaret A. "Handbook of diabetes medical nutrition therapy". Jones & Bartlett Learning, 1996, pp. 482-483.*

* cited by examiner

PREDICTING GLUCOSE TRENDS FOR POPULATION MANAGEMENT

BACKGROUND

Diabetes patients traditionally face two dangerous types of critical situations. The first situation, hypoglycemia, is characterized by abnormally low blood glucose (blood sugar) levels and is often referred to as hypoglycemia. Patients experiencing severe hypoglycemia may suffer accidents, injuries, coma, and death. The second situation, hyperglycemia, is characterized by abnormally high blood glucose and may occur when a patient has too little insulin or is unable to use insulin properly. Untreated hyperglycemia may result in ketoacidosis (diabetic coma). Unfortunately, clinicians treating diabetes patients are not able to effectively predict or prevent either situation.

BRIEF SUMMARY

Embodiments of the present invention generally relate to building and using a predictive model based on discrete information for multiple patients from multiple venues to identify persons at risk of developing an abnormal blood glucose level. The venues may include care facilities, laboratories, and residences. The information may include glucose data including context data and demographic data associated with the glucose data. For example the glucose data may include clinical information, disease burden, utilization cost, demographics and characteristics, diagnostic values, medications, or environmental and social data. One or more predictive models may be built, for instance, by using one or more logistic or linear regression models to identify the most relevant data to predict a likelihood of a particular patient to have abnormally high or abnormally low glucose levels. A prediction and one or more interventions may be communicated to a care team or the particular patient based on the likelihood. The one or more interventions may be incorporated into a clinical device workflow associated with a clinician on the care team or the patient.

Accordingly, in one aspect, an embodiment of the present invention is directed to one or more computer storage media storing computer-useable instructions that, when used by one or more computing devices, cause the one or more computing devices to perform operations. The operations include receiving glucose data at a prediction server. The glucose data received from a plurality of sources includes an electronic medical record associated with a patient, one or more care facilities, one or more laboratories, or one or more integrated home devices. The operations further include determining, based on the glucose data, a real-time prediction indicating whether the patient is trending to have dangerous blood glucose levels. The operations further include communicating, based on the determining, the real-time prediction and one or more interventions to a care team or the patient.

In another embodiment, an aspect is directed to a computer-implemented method in a clinical computing environment. The method includes receiving, via a first computing process, glucose data for a plurality of patients from a plurality of sources. The glucose data includes context data and demographic data associated with the glucose data and the plurality of patients. The method also includes generating, via a second computing process, a predictive model based on the glucose data using one or more logistic or linear regression models. The method further includes employing, via a third computing process, the predictive model to predict a likelihood of a particular patient to have dangerous blood glucose levels. The method further includes communicating, via a fourth computing process, a prediction and one or more interventions to a care team and the patient based on the likelihood. The method further includes incorporating, via a fifth computing process, the one or more interventions into a clinical device workflow associated with a clinician on the care team. Each of the computing processes is performed by one or more computing devices.

A further embodiment is directed to a system comprising: a glucose database storing glucose data received for a plurality of patients from a plurality of sources, the glucose data including context data and demographic data associated with the glucose data and the plurality of patients; one or more processors; and one or more computer storage media storing instructions that, when used by the one or more processors, cause the one or more processors to: generate one or more predictive models based on the glucose data using one or more logistic or linear regression models; employ the one or more predictive models to predict a likelihood of a particular patient to have dangerous blood glucose levels; and communicate a prediction and one or more interventions to a care team based on the likelihood.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE SEVERAL VIEWS OF THE DRAWINGS

The present invention is described in detail below with reference to the attached drawing figures, wherein.

DETAILED DESCRIPTION

Figure 1:
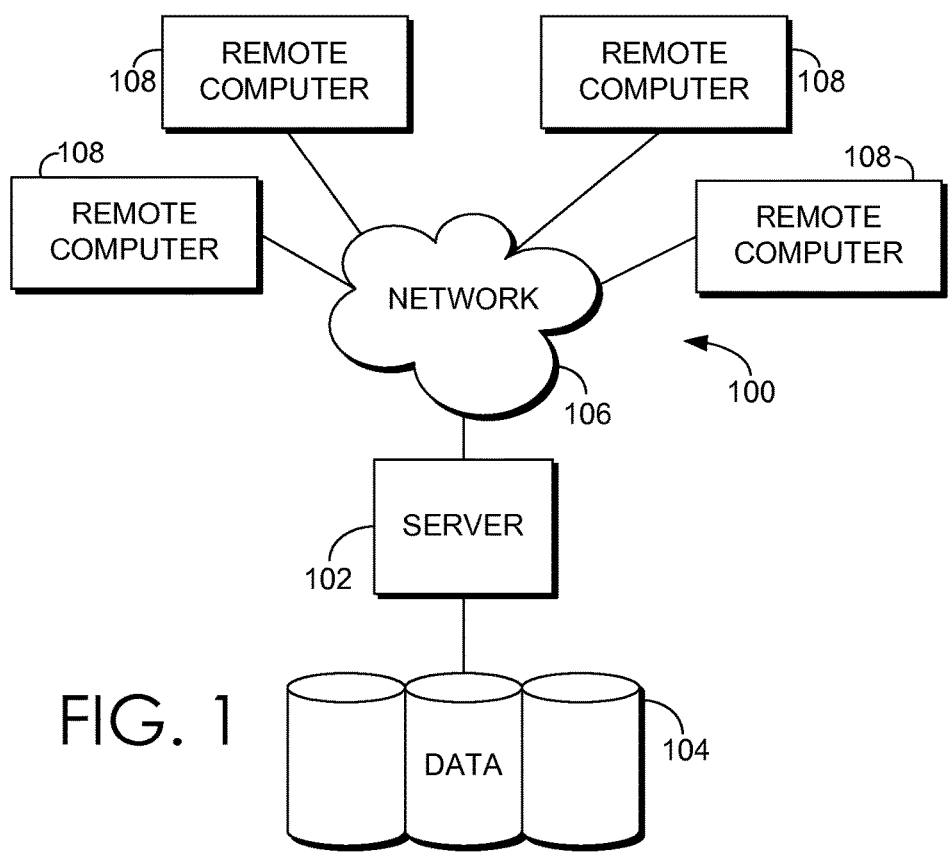
FIG. 1 is a block diagram of an exemplary computing environment suitable for use in implementing the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Diabetes is the seventh leading cause of death in the United States. The cost of treating and managing diabetes is estimated at approximately two hundred forty billion dollars per year. Extremely high (e.g., >240 mg/dL) and extremely low (e.g., <70 mg/dL) blood glucose levels are highly associated with both acute and long term morbidity and mortality. Preventing these extreme events can improve patient outcomes and lower medical costs.

Current clinical systems that are utilized to treat diabetes patients are tailored to utilize current data, such as from an insulin pump, to control the insulin pump in accordance with an actual low or high level of blood glucose corresponding to the current data. These systems are based on a general understanding of physiologies, such as production of insulin and decay rate, and interpolating what is currently happening to the patient. Unfortunately, these systems rely on this general understanding and treat all patients in the same manner. Further, these systems do not capture data that can predict when these dangerous types of situations are likely to occur. Rather, the current systems react to when the situations are occurring. Still further, only a small fraction of those suffering from diabetes have actually been diagnosed or are being treated with insulin pumps and a large population of undiagnosed or untreated patients remain at risk.

Embodiments of the present invention are generally directed to computerized methods and systems that provide for predicting glucose trends for population management. A predictive model may be automated to provide real-time information tailored narrowly to the unique needs of an individual patient. When the patient is at an increased risk of crossing into an extreme blood glucose level, alerts may be generated. In an acute care setting, a clinician can take steps to prevent the extreme blood glucose level from occurring. In a self-monitoring setting, the patient can take steps to prevent the extreme blood glucose level from occurring. The availability of predictive information facilitates preventative actions for individuals and system awareness for the care of a population of diabetics. The link between the data, the predictive model, and the workflow provides a more efficient, accurate, and timely care of diabetes patients. Additionally, home environment and community related situations and/or data, may also contribute to fluctuation and trending of glucose level. Such information, when correlated with known clinical information from history and longitudinal record, will add strength to such a model as well as provide information on the best engagement opportunities and appropriate interventions to prevent a potentially dangerous situation.

Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a general purpose computing device in the form of a server 102. Components of the server 102 may include, without limitation, a processing unit, internal system memory, and a suitable system bus for coupling various system components, including database cluster 104, with the server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 102 typically includes, or has access to, a variety of computer readable media, for instance, database cluster 104. Computer readable media can be any available media that may be accessed by server 102, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 102. Computer storage media does not comprise signals per se. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 104, provide storage of computer readable instructions, data structures, program modules, and other data for the server 102.

The server 102 may operate in a computer network 106 using logical connections to one or more remote computers 108. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 108 may also be physically located in non-traditional medical care environments so that the entire health care community may be capable of integration on the network. The remote computers 108 may be personal computers, servers, routers, network PCs, peer devices, other common network nodes, or the like, and may include some or all of the components described above in relation to the server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the server 102 may include a modem or other means for establishing communications over the WAN, such as the Internet. In a networked environment, program modules or portions thereof may be stored in the server 102, in the database cluster 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In operation, a user may enter commands and information into the server 102 or convey the commands and information to the server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 102. In addition to a monitor, the server 102 and/or remote computers 108 may include other peripheral output devices, such as speakers and a printer.

Although many other internal components of the server 102 and the remote computers 108 are not shown, those of ordinary skill in the art will appreciate that such components and their interconnection are well known. Accordingly, additional details concerning the internal construction of the server 102 and the remote computers 108 are not further disclosed herein.

Figure 2:
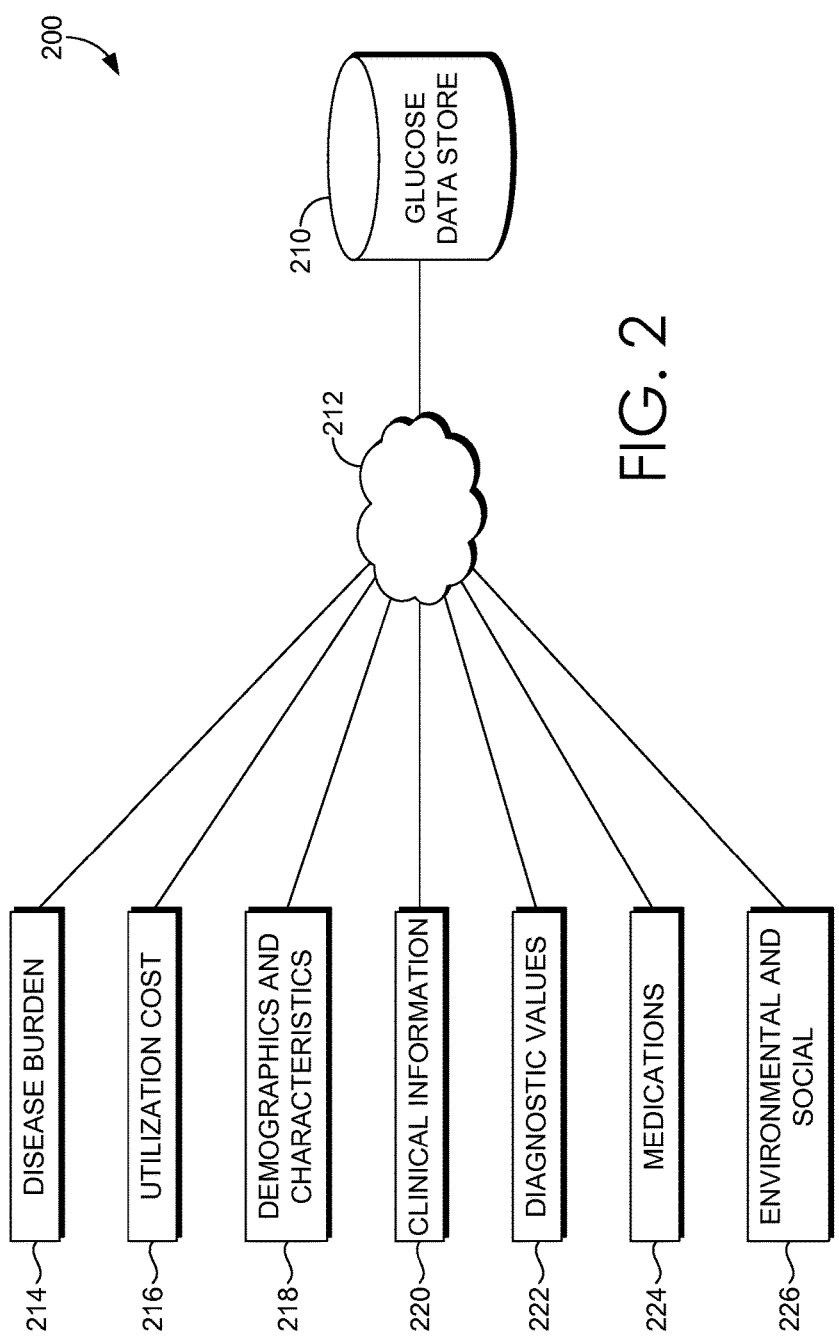
FIG. 2 is a block diagram of an exemplary system for storing glucose data used by one or more logistic or linear regression models to generate one or more predictive models in accordance with an embodiment of the present invention.

In FIG. 2, a block diagram of an exemplary system for storing glucose data used by one or more logistic or linear regression models to generate one or more predictive models in accordance with an embodiment of the present invention is shown. Glucose data store 210 comprises a plurality of elements received from a plurality of sources via a network 212. The sources may include an EMR associated with a patient, one or more care facilities, one or more laboratories, or one or more integrated home devices. For example, the glucose data may include disease burden 214 for a patient. The disease burden 214 indicates whether any comorbidities exist for a particular patient (i.e., a presence of a disease or condition in addition to diabetes).

The glucose data may also include utilization cost 216. The utilization cost includes data regarding previous visits. For example, the utilization cost may indicate the time of day, day of the week, month, and the like, for previous visits associated with a patient.

Referring now to FIG. 2, a block diagram is provided illustrating exemplary data elements that are communicated via network 212 and stored in glucose database 210. Each of these data elements may be analyzed, using various machine learning techniques, to identify data elements that may indicate trends for patients having dangerous blood glucose levels. In this regard, the glucose database 210 may be refined and tailored utilizing some or all of the data elements in addition to other data elements that may be associated with these trends. The exemplary data elements may include disease burden 214, utilization cost 216, demographics and characteristics 218, clinical information 220, diagnostic values 222, medications 224, and/or environmental and social 226.

Disease burden 214 data element may include comorbidities. The comorbidities may indicate the presence of one or more disorders or diseases that are associated with a higher risk of a patient also having dangerous blood glucose levels. Utilization cost 216 may include data associated with previous visits or laboratory draws. For example, the time of day or month of a previous visit or laboratory draw may be included in the utilization cost 216. Demographics and characteristics 218 may include age, gender, and/or race. Clinical information 220 includes clinical data such as a diagnosis, for example, retrieved from the EMR. Diagnostic values 222 include glucose laboratory results that may be retrieved, for example, from the EMR. Medications 224 may include any medications retrieved, for example, from the EMR or insurance claims. Environmental and social 226 may include marital status, facility type, and the like.

Figure 3:
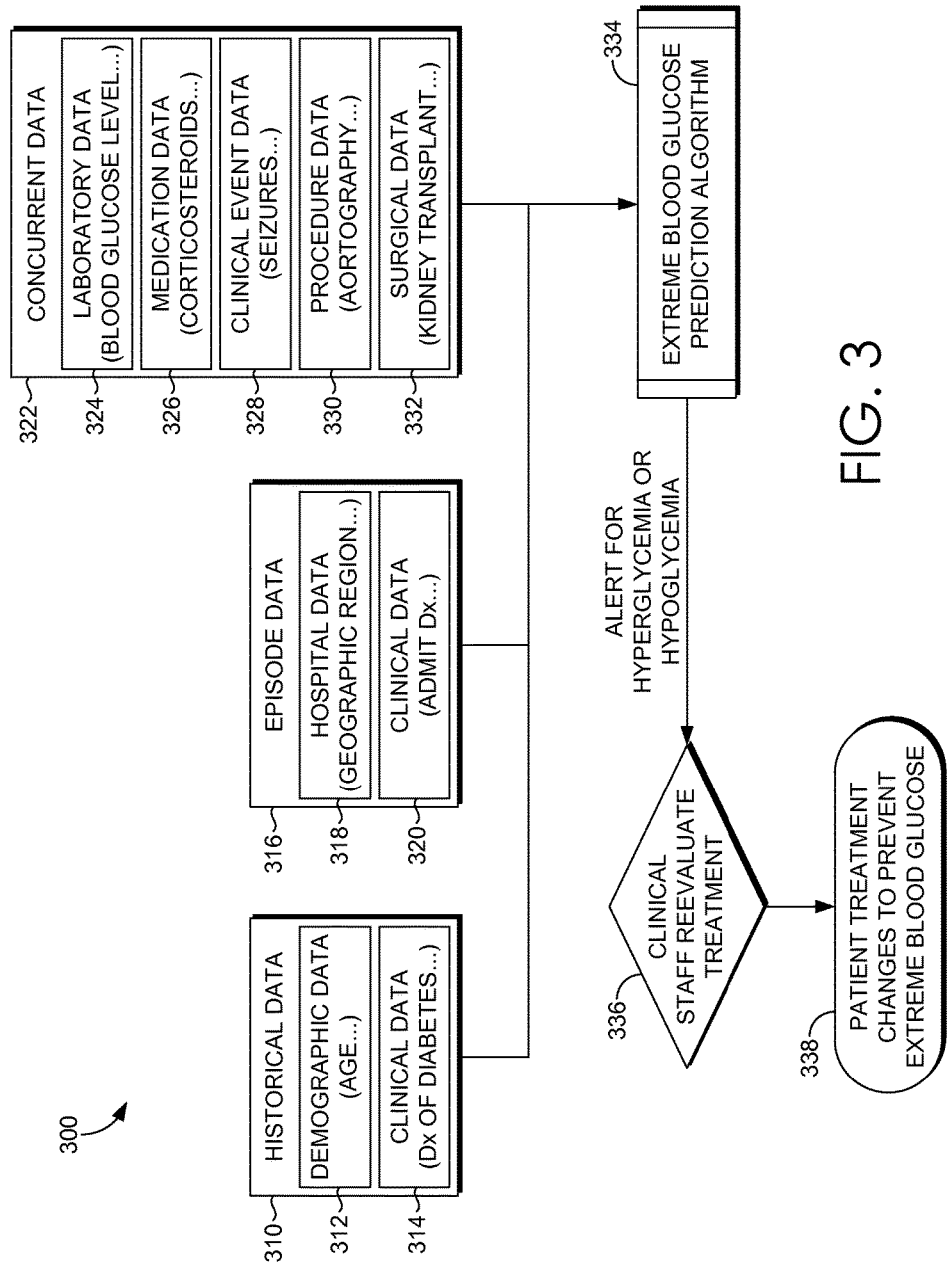
FIG. 3 is a flow diagram showing a method for utilizing a predictive model to prevent dangerous blood glucose levels in accordance with an embodiment of the present invention.

Referring now to FIG. 3, a flow diagram of a method 300 for utilizing a predictive model to prevent dangerous blood glucose levels in accordance with an embodiment of the present invention is shown. Historical data 310, episode data 316, and concurrent data 322 may be stored in an EMR associated with a patient, received from one or more care facilities, received from one or more laboratories, and/or received from one or more integrated home devices. Historical data 310 may include demographic data 312 (e.g., age) and/or clinical data 314 (e.g. a diagnosis). Episode data 316 may include hospital data 318 (e.g., geographic region) and/or clinical data 320 (e.g., admit diagnosis). Concurrent data 322 may include laboratory data 324 (e.g., blood glucose level), medication data 326 (e.g., indicating a patient is taking corticosteroids), clinical event data 328 (e.g., indicating a patient suffers from seizures), procedure data 330 (e.g., a patient is undergoing an aortography), and/or surgical data 332 (e.g., a patient is having or had a kidney transplant).

Each of the data elements comprised by historical data 310, episode data 316, and concurrent data 322 may be communicated, in any combination or individually to extreme blood glucose prediction algorithm 334. The extreme blood glucose prediction algorithm 334 provides an alert if a particular patient is predicted to be hyperglycemic or hypoglycemic. If an alert is provided, at step 336, the clinical staff reevaluates treatment. The patient treatment changes to prevent extreme blood glucose at step 338. Although only a single predictive algorithm is shown in FIG. 3, it should be understood that any number of predictive algorithms may be generated. Prediction server 410, described below with respect to FIG. 4, employs the predictive algorithm 334 in association with the historical data 310, episode data 316, and concurrent data 322 to predict a likelihood of a particular patient to have dangerous blood glucose levels.

Figure 7:
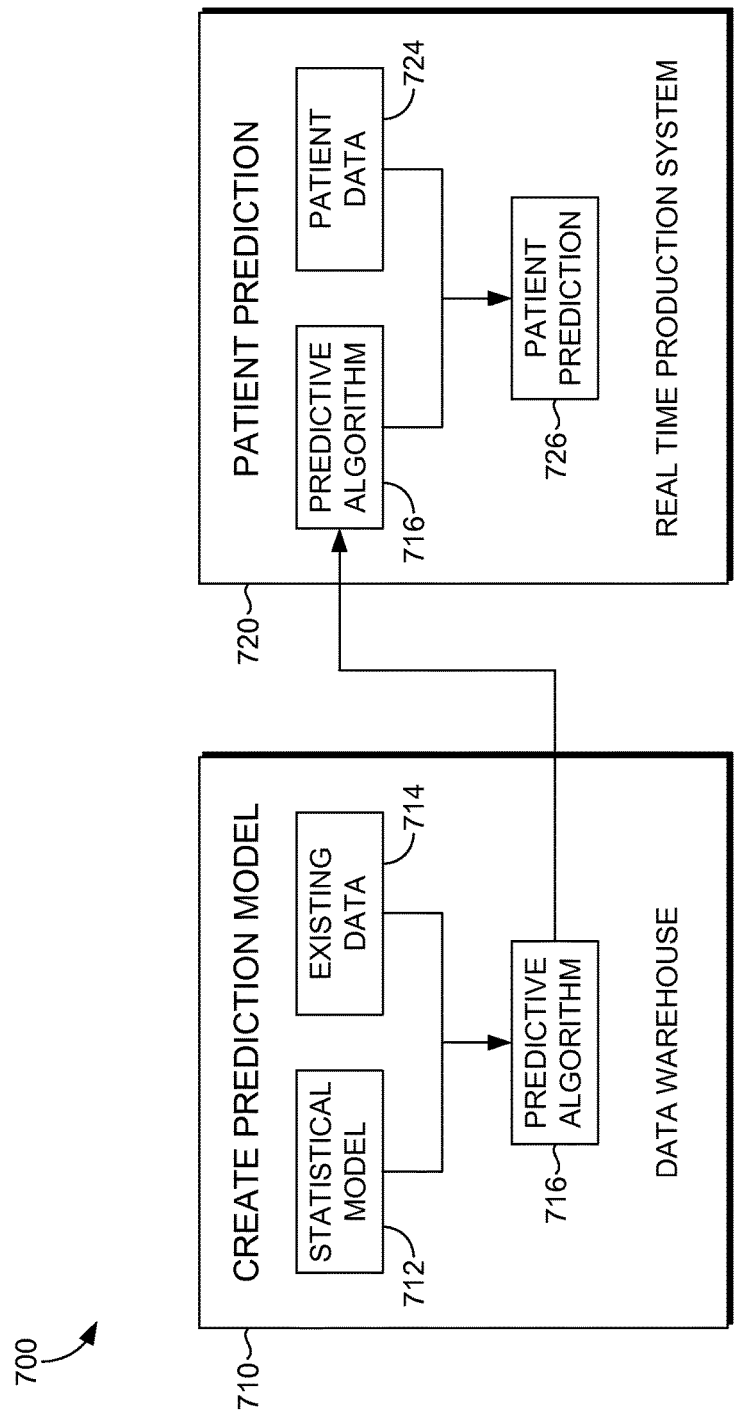
FIG. 7 is a block diagram of an exemplary system for creating the one or more logistic or linear regression models to generate one or more predictive algorithms utilized for patient prediction in accordance with an embodiment of the present invention.

In FIG. 7, a block diagram block diagram of an exemplary system 700 for creating the one or more logistic or linear regression models to generate one or more predictive algorithms utilized for patient prediction is shown in accordance with an embodiment of the present invention. In the create prediction model 710, a statistical model 712 is trained using existing data 714 (which may be stored in a data warehouse) to produce a predictive algorithm 716. In the patient production 720, the predictive algorithm 716 utilizes patient data 724 (which may include real-time data) to produce a patient prediction 726.

Figure 4:
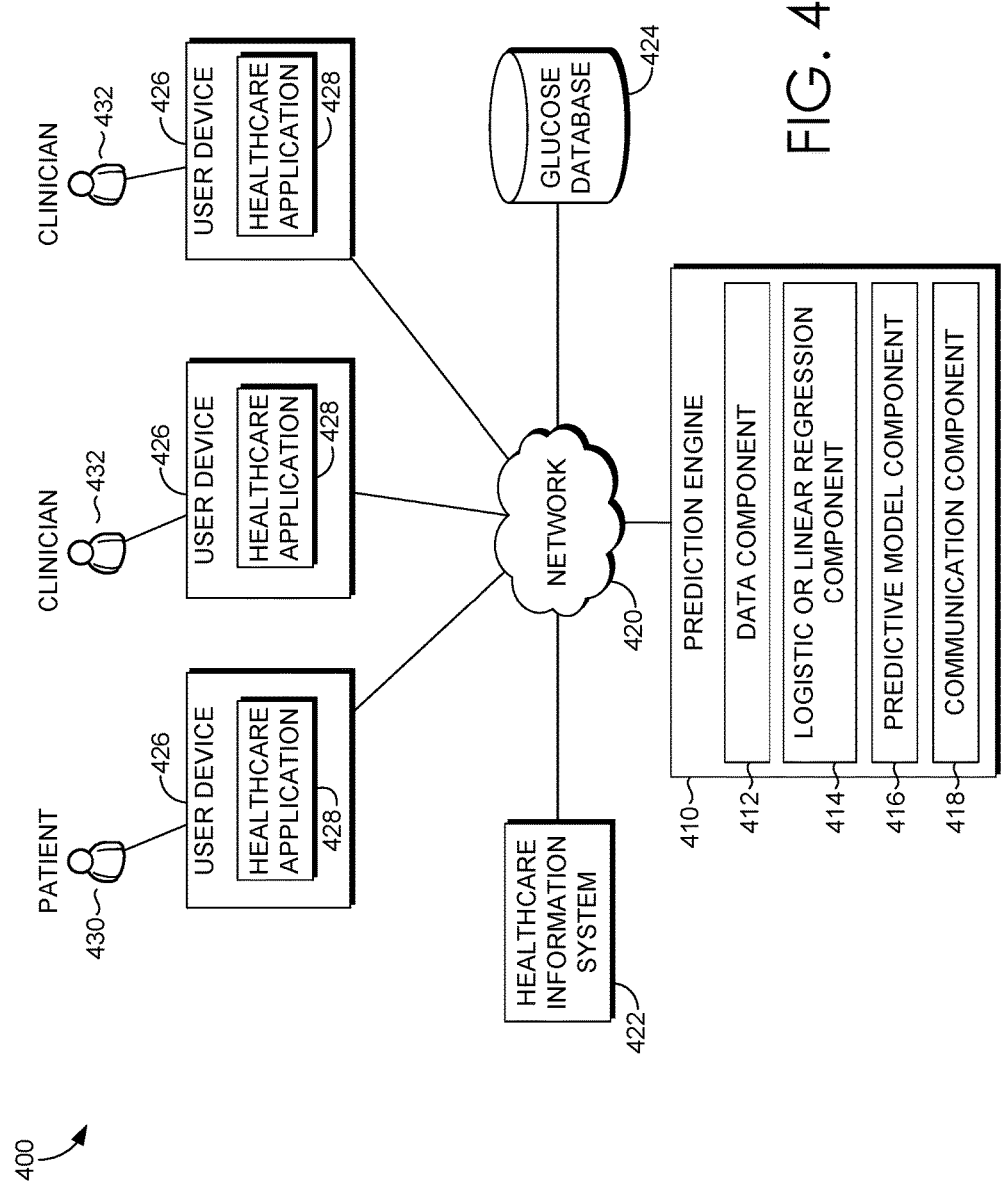
FIG. 4 is a block diagram of an exemplary system for using a predictive model to predict the likelihood of dangerous blood glucose levels in accordance with embodiments of the present invention.

FIG. 4 provides a block diagram illustrating an exemplary system 400 in which a predictive server 410 is used to build a predictive model in accordance with embodiments of the present invention. The predictive model is used to predict a likelihood of a particular patient to have dangerous blood glucose levels. As shown in FIG. 4, a healthcare application 428 is provided on a user device 426 that may be accessible by a patient 430 or one or more clinicians 432. The healthcare application 428 may generally be any software that allows the patient or one or more clinicians to provide information to the predictive server 410 via a network 420 and/or receive alerts, interventions, workflows, and the like. Each of the predictive server 410 and the user devices 426 may be connected via the network 420 to healthcare information system 422. The healthcare information system 422 may similarly provide information to or receive information from the predictive server 410 and user devices 426 via the network 420.

Glucose database 424 stores glucose data used by prediction server 410 to generate one or more predictive models in accordance with an embodiment of the present invention. Glucose database 424 comprises a plurality of elements received from a plurality of sources via a network 420, including elements received from healthcare information system 422 and user devices 426. The sources may additionally include an EMR associated with a patient, one or more care facilities, one or more laboratories, or one or more integrated home devices.

As described above, the exemplary data elements may include disease burden, utilization cost, demographics and characteristics, clinical information, diagnostic values, medication data, and/or environmental and social data. Disease burden may include comorbidities. The comorbidities may indicate the presence of one or more disorders or diseases that are associated with a higher risk of a patient also having dangerous blood glucose levels. Utilization cost may include data associated with previous visits or laboratory draws. For example, the time of day or month of a previous visit or laboratory draw may be included in the utilization cost. Demographics and characteristics may include age, gender, and/or race. Clinical information includes clinical data such as a diagnosis, for example, retrieved from the EMR. Diagnostic values include glucose laboratory results that may be retrieved, for example, from the EMR. Medications may include any medications retrieved, for example, from the EMR or insurance claims. Environmental and social 226 may include marital status, facility type, and the like.

Prediction engine 410 employs a predictive model (e.g., a predictive model generated by the predictive model component 416) to predict a likelihood of a particular patient to have dangerous blood glucose levels. While the predication server 410 is shown separate from the user device 426, in some embodiments, the prediction server may be provided locally on the user device 426. In other embodiments, the prediction engine 410 may be provided remotely from the user device 426. For instance, the prediction engine 410 may be provided as a cloud-based service.

In some embodiments, the data component 412 of the prediction engine 410 may retrieve and analyze the data elements stored in glucose database 424 as well as data received from healthcare information system 422 and user devices 426. These data elements may be communicated to logistic or linear regression component 414 to generate one or more predictive models based on the glucose data using one or more logistic or linear regression models. As can be appreciated the logistic or linear regression component 414 may use one or more logistic equations to identify one or more correlations between one or more data elements and dangerous glucose levels. Once identified, predictive model component 416 may employ the one or more predictive models to predict a likelihood of a particular patient to have dangerous blood glucose levels. Communication component 418 communicates a prediction and one or more interventions to a care team or the particular patient based on the likelihood. In embodiments, a context based predictive model of the one or more predictive models may be determined to employ for the particular patient. In this case, the predictive model may be specifically relevant to the particular patient.

Figure 5:
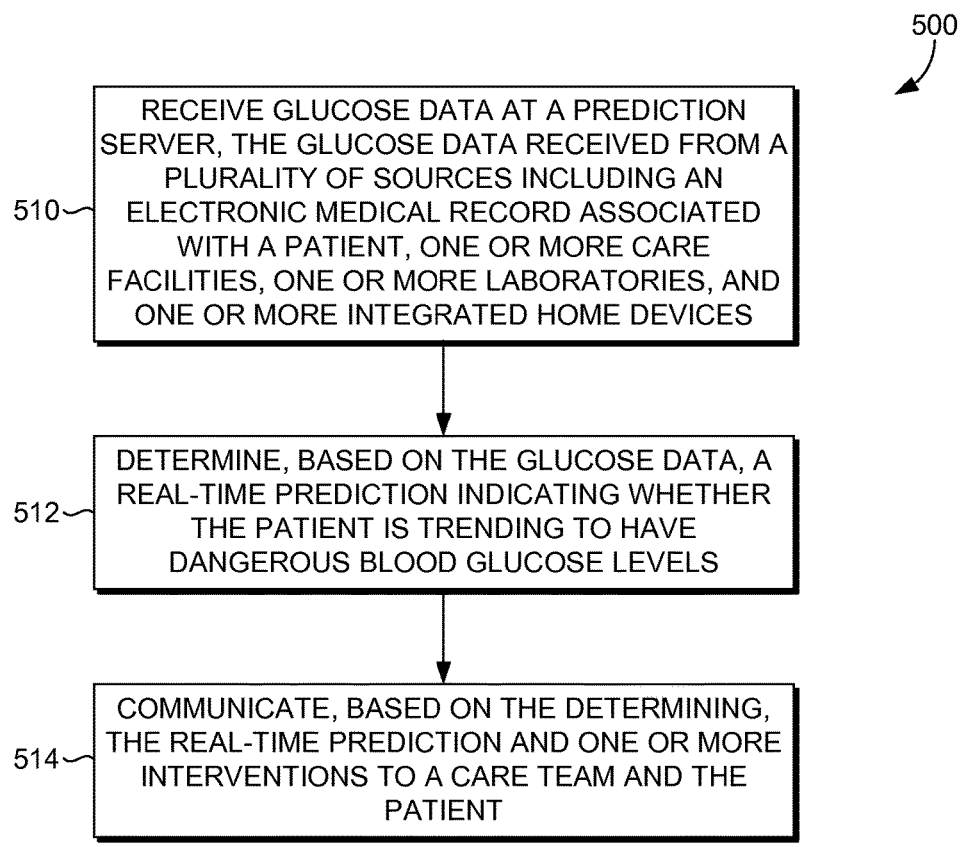
FIG. 5 is a flow diagram showing a method for communicating a real-time prediction and one or more interventions in accordance with an embodiment of the present invention.

Turning now to FIG. 5, a flow diagram is provided that illustrates a method 500 for communicating a real-time prediction and one or more interventions in accordance with an embodiment of the present invention. As shown at block 510, glucose data is received at a prediction server. The glucose data may be received from a plurality of sources including an EMR associated with a patient, one or more care facilities, one or more laboratories, and one or more integrated home devices. For example, the glucose data may include historical data, episode data, and/or concurrent data. The historical data may include demographic data (e.g., age, race, gender) and/or clinical data (e.g., a diagnosis). The episode data may include hospital data (e.g., geographic region) and/or clinical data (e.g., admit diagnosis). The concurrent data may include laboratory data (e.g., blood glucose level), medication data (e.g., indicating a patient is taking corticosteroids), clinical event data (e.g., indicating a patient suffers from seizures, procedure data (e.g., a patient is undergoing an aortography), and/or surgical data (e.g., a patient is having or had a kidney transplant). Each of the data elements comprised by historical data, episode data, and concurrent data may be received, in any combination or individually at the prediction server.

At block 512, a real-time prediction is determined, based on the glucose data, indicating whether the patient is trending to have dangerous blood glucose levels. The real-time prediction and one or more interventions are communicated, at block 514, to a care team and the patient. The one or more interventions may be a workflow specific to glucose data associated with the patient that may help reverse the trend. The workflow may be steps for the patient to follow, steps for a clinician to follow, and/or steps for both the patient and the clinician to follow.

In some embodiments, a predictive model may be generated based on data from a single healthcare provider, facility, or population. Using data from a single provider, facility, or population may allow a model tailored more specifically to a particular patient. In other embodiments, data from multiple healthcare providers, facilities, or populations may be used. Using data from multiple healthcare providers, facilities, or populations may allow for more information to provide a more accurate model.

In some embodiments, the real-time prediction is based on a prediction model using logistic or linear regression models. For example, each of the data elements describe above may be analyzed, using logistic or linear regression models or other machine learning techniques, to identify the data elements indicating trends for patients having dangerous blood glucose levels. The prediction model predicts whether the patient is likely to have abnormally high or abnormally low glucose levels.

The prediction model that predicts whether the patient is likely to have abnormally high glucose levels may leverage the glucose data including: a most recent glucose lab value; a month, a time, and a year the most recent glucose lab value was drawn; whether the most recent glucose lab value was drawn on a weekend; and an age, marital status, and race of the patient. The prediction model that predicts whether the patient is likely to have abnormally low glucose levels may leverage the glucose data including: a most recent glucose lab value; a month, a time, and a year the most recent glucose lab value was drawn; whether the most recent glucose lab value was drawn on a weekend; and an age and race of the patient; geographic region where the most recent lab value was drawn; and whether the most recent lab value was drawn at a teaching facility.

The real-time prediction and one or more interventions are communicated, at block 514, to a care team and the patient. In some embodiments, the interventions are incorporated into a workflow provided on a clinical device associated with a clinician on the care team. The interventions may include specific recommended actions (e.g., treatments, medications, and the like). In some embodiments, medication levels associated with the one or more integrated home devices may be automatically adjusted. For example, an intervention may indicate a dosage or frequency medication the patient is currently taking via an integrated home device should be increased or decreased. In this case, the medication level can be automatically adjusted by communicating the dosage or frequency change to the integrated home device.

In some embodiments, additional data is received from the care team and the patient. The additional data may be utilized to update the real-time prediction and the interventions. The additional data may include items associated with previous interventions and, once utilized, may indicate the patient is no longer trending to have dangerous blood glucose levels. In one embodiment, the additional data includes data received from the patient in an electronic questionnaire communicated to the patient as at least a portion of the intervention.

Figure 6:
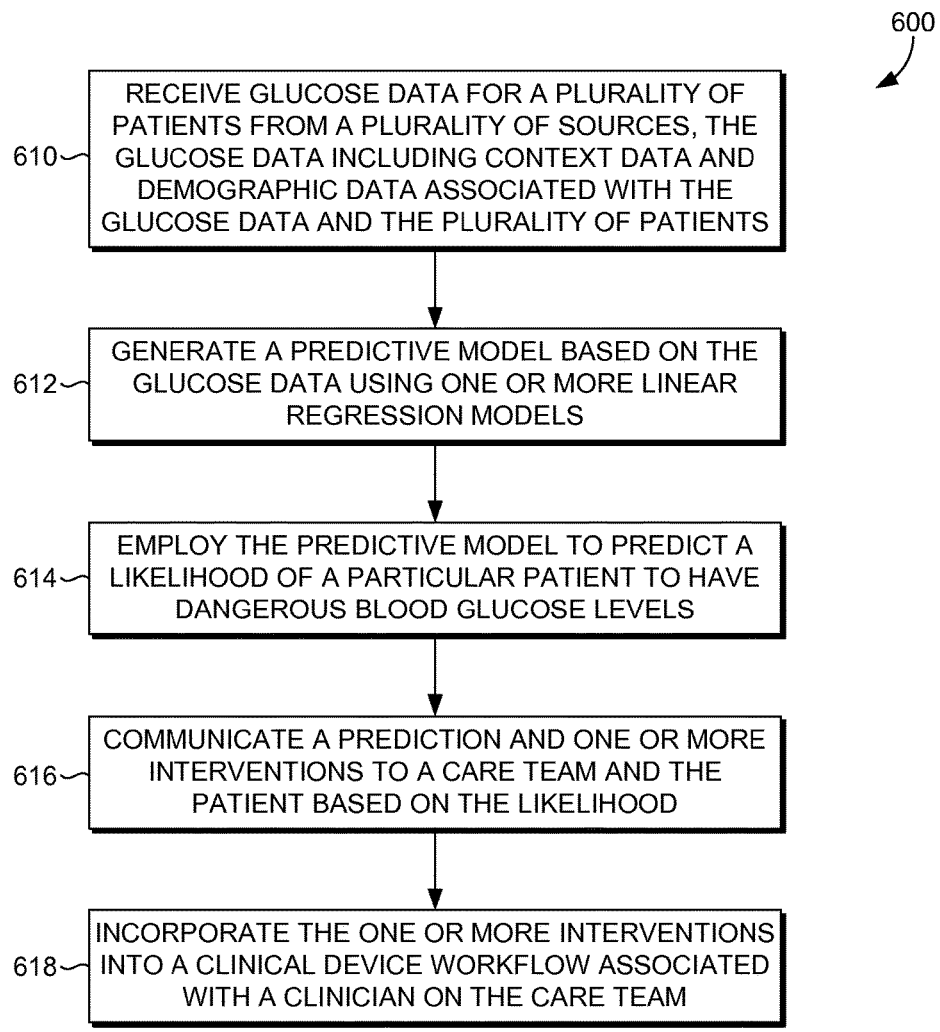
FIG. 6 is a flow diagram showing a method for using a predictive model to incorporate one or more interventions into a clinical device workflow in accordance with an embodiment of the present invention.

With reference now to FIG. 6, a flow diagram is provided that illustrates a method 600 for using a predictive model to incorporate one or more interventions into a clinical device workflow in accordance with an embodiment of the present invention. As shown at block 610, glucose data is received for a plurality of patients from a plurality of sources. The glucose data includes context data and demographic data associated with the glucose data and the plurality of patients. The glucose data may be received (i.e., by data component 412 of FIG. 4) from a glucose data store (e.g., glucose database 424 of FIG. 4).

A predictive model is generated, at block 612, based on the glucose data using one or more logistic or linear regression models (e.g., by logistic or linear regression component 414 of FIG. 4). As can be appreciated, various logistic or linear regression models may be generated utilizing more general glucose data from a larger population of patients (e.g., males and females living in the United States), or can be specifically tailored to a particular type of patient by utilizing more specific glucose data from a more specific population of patients (e.g., Caucasian males living in Missouri between the ages of 40 and 50 that have been prescribed a particular medication).

At block 614, the predictive model is employed to predict a likelihood of a particular patient to have dangerous blood levels (e.g., by predictive model component 416 of FIG. 4). In some embodiments, the glucose data associated with the predictive model to predict a likelihood of a particular patient to have abnormally high glucose levels includes: a most recent glucose lab value; a month, a time, and a year the most recent glucose lab value was drawn; whether the most recent glucose lab value was drawn on a weekend; and an age, marital status, and a race. In some embodiments, the glucose data associated with the predictive model to predict a likelihood of a particular patient to have abnormally low glucose levels includes: a most recent glucose lab value; a month, a time, and a year the most recent glucose lab value was drawn; whether the most recent glucose lab value was drawn on a weekend; and an age and race of the patient; geographic region where the most recent lab value was drawn; and whether the most recent lab value was drawn at a teaching facility. Alternatively or additionally, the glucose data associated with the predictive model to predict a likelihood of a particular patient to have abnormally low glucose levels may include: diagnoses, past and current medications, laboratory results other than blood glucose levels, clinical events observed, and medical procedures performed.

A prediction and one or more interventions is communicated, at block 616, to a care team and the patient based on the likelihood of the patient having dangerous blood glucose levels (e.g., by communication component 418 of FIG. 4). The one or more interventions are incorporated, at block 618, into a clinical device workflow associated with a clinician on the care team. The one or more interventions may include automatically adjusting medication levels associated with one or more integrated home devices. In some embodiments, an electronic questionnaire may be communicated to the patient in association with the one or more interventions.

In some embodiments, additional data is received from the care team and the patient. The additional data may be data that results from the one or more interventions being performed by the clinician and/or the patient. For example, the intervention may be an increase or decrease in an insulin dose, instructions to eat additional calories, or an order for laboratories. By performing one or more interventions, the additional data may be employed by the predictive model to update the real-time prediction and clinical device workflow.

As can be understood, embodiments of the present invention provide for the generation of predictive models based on glucose data and use of the predictive models to predict the whether a patient is trending to have dangerous blood glucose levels. Although the present invention is described in the context of blood glucose levels, predictive models could similarly be generated and utilized to predict whether a patient is likely to develop pneumonia or sepsis. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more computer storage media storing computer-useable instructions, the instructions when executed by one or more computing devices, cause the one or more computing devices to perform operations comprising:
    receiving a first set of glucose data at a prediction server, the first set of glucose data received from a plurality of sources including electronic medical records associated with a plurality of patients, one or more care facilities, one or more laboratories, or one or more integrated home devices;
    generating, based on at least the glucose data, a training data set;
    training, based on the training data set, one or more predictive models by determining one or more trends in the training data;
    receiving, from a glucose monitor, a second set of glucose data corresponding to a patient;
    determining, based on the second set of glucose data and utilizing the one or more predictive models, a real-time prediction indicating whether the patient is likely to have blood glucose levels corresponding to a predetermined threshold;
    communicating, based on the determining, the real-time prediction and one or more interventions to a care team and the patient; and
    automatically adjusting a frequency or dosage of medication dispensed by an integrated home device associated with the patient based on the one or more interventions.

2. The one or more computer storage media of claim 1, the operations further comprising receiving additional data from the care team and the patient.

3. The one or more computer storage media of claim 2, the operations further comprising utilizing the additional data to update the real-time prediction and the interventions.

4. The one or more computer storage media of claim 3, wherein the prediction model that predicts whether the patient is likely to have >240 mg/dL glucose levels leverages the glucose data including: a most recent glucose lab value; a month, a time, and a year the most recent glucose lab value was drawn; whether the most recent glucose lab value was drawn on a weekend; and an age, marital status, and race of the patient.

5. The one or more computer storage media of claim 3, wherein the prediction model that predicts whether the patient is likely to have <70 mg/dL glucose levels leverages the glucose data including: a most recent glucose lab value; a month, a time, and a year the most recent glucose lab value was drawn; whether the most recent glucose lab value was drawn on a weekend; and an age and race of the patient; geographic region where the most recent lab value was drawn; and whether the most recent lab value was drawn at a teaching facility.

6. The one or more computer storage media of claim 2, wherein the prediction model predicts whether the patient is likely to have >240 mg/dL or <70 mg/dL glucose levels.

7. The one or more computer storage media of claim 2, wherein the additional data includes data received from the patient in an electronic questionnaire communicated to the patient as at least a portion of the intervention.

8. The one or more computer storage media of claim 1, wherein the prediction model comprises one or more logistic or linear regression models.

9. The one or more computer storage media of claim 1, the operations further comprising incorporating the interventions into a workflow provided on a clinical device associated with a clinician on the care team.

10. The one or more computer storage media of claim 1, wherein the interventions include specific recommended actions.

11. A computer-implemented method in a clinical computing environment comprising:
    receiving, via a first computing process, glucose data for a plurality of patients from a plurality of sources, the glucose data including context data and demographic data associated with the glucose data and the plurality of patients;
    generating, via a second computing process, a predictive model based on the glucose data using one or more logistic or linear regression models;
    employing, via a third computing process, the predictive model to predict a likelihood of a particular patient to have blood glucose levels corresponding to a predetermined threshold;
    communicating, via a fourth computing process, a prediction and one or more interventions to a care team and the patient based on the likelihood;
    automatically adjusting a frequency or dosage of medication dispensed by an integrated home device associated with the patient based on the one or more interventions; and
    incorporating, via a fifth computing process, the one or more interventions into a clinical device workflow associated with a clinician on the care team;
    wherein each of the computing processes is performed by one or more computing devices.

12. The method of claim 11, wherein the glucose data associated with the predictive model to predict a likelihood of a particular patient to have >240mg/dL glucose levels includes: a most recent glucose lab value; a month, a time, and a year the most recent glucose lab value was drawn; whether the most recent glucose lab value was drawn on a weekend; and an age, marital status, and a race.

13. The method of claim 11, wherein the glucose data associated with the predictive model to predict a likelihood of a particular patient to have <70mg/dL glucose levels includes: a most recent glucose lab value; a month, a time, and a year the most recent glucose lab value was drawn; whether the most recent glucose lab value was drawn on a weekend; and an age and race of the patient; geographic region where the most recent lab value was drawn; and whether the most recent lab value was drawn at a teaching facility.

14. The method of claim 11, further comprising receiving, via a sixth computing process, additional data from the care team and the patient.

15. The method of claim 14, further comprising updating, via a seventh computing process, the real-time prediction and clinical device workflow based on the additional data.

16. The method of claim 11, further comprising communicating, via a ninth computing process, an electronic questionnaire to the patient in association with the one or more interventions.

17. A system comprising:
a glucose database storing glucose data received for a plurality of patients from a plurality of sources, the glucose data including context data and demographic data associated with the glucose data and the plurality of patients;
one or more processors; and
one or more computer storage media storing instructions, the instructions when executed by the one or more processors, cause the one or more processors to:
generate one or more predictive models based on the glucose data using one or more logistic or linear regression models;
employ the one or more predictive models to predict a likelihood of a particular patient to have blood glucose levels corresponding to a predetermined threshold;
communicate a prediction and one or more interventions to a care team or the particular patient based on the likelihood; and
communicate a frequency or dosage of medication change to an integrated home device associated with the particular patient based on the one or more interventions.

18. The system of claim 17, wherein the instructions when executed by the one or more processors further cause the one or more processors to:
determine a context based predictive model of the one or more predictive models to employ for the particular patient.

* * * * *